United States Patent
Di Fiore et al.

(10) Patent No.: US 6,514,262 B1
(45) Date of Patent: Feb. 4, 2003

(54) DERMABRASION BY A FLOW OF REDUCING SUBSTANCES AND HAVING DISPOSABLE STERILIZED COMPONENTS

(75) Inventors: Dario Di Fiore, Florence (IT); Carlo Stanisci, Florence (IT)

(73) Assignee: Mattioli Engineering Ltd., London (GB)

( * ) Notice: Subject to any disclaimer, the term of this patent is extended or adjusted under 35 U.S.C. 154(b) by 26 days.

(21) Appl. No.: 09/614,905

(22) Filed: Jul. 12, 2000

Related U.S. Application Data

(63) Continuation-in-part of application No. 09/099,523, filed on Jun. 18, 1998, now Pat. No. 6,306,141, which is a continuation-in-part of application No. 09/088,873, filed on Jun. 2, 1998, now abandoned, which is a continuation-in-part of application No. 08/797,909, filed on Feb. 10, 1997, now Pat. No. 6,120,512, which is a continuation-in-part of application No. 08/496,470, filed on Jun. 29, 1995, now Pat. No. 5,810,842.

(30) Foreign Application Priority Data

Jun. 29, 1994 (IT) ............................................. FI94A0131
Feb. 10, 1996 (IT) ............................................. FI96A0108

(51) Int. Cl.[7] .............................................. A61B 17/50
(52) U.S. Cl. ..................... 606/131; 604/94.01; 604/275
(58) Field of Search .......................... 606/131, 1, 167; 604/19, 22, 35, 82, 289, 310, 313, 902; 51/293–309; 510/101, 130, 132, 136–139, 155, 159–161, 405, 406

(56) References Cited

U.S. PATENT DOCUMENTS

| | | | |
|---|---|---|---|
| 931,348 A | | 8/1909 | Schulz |
| 1,452,274 A | | 4/1923 | Houskeeper |
| 1,643,886 A | | 9/1927 | Goodman |
| 4,685,328 A | | 8/1987 | Huebner et al. |
| 5,013,240 A | * | 5/1991 | Bailey et al. ................... 433/77 |
| 5,037,431 A | | 8/1991 | Summers et al. ............ 606/131 |
| 5,037,432 A | * | 8/1991 | Molinari ...................... 606/131 |
| 5,100,412 A | * | 3/1992 | Rosso ......................... 606/131 |
| 5,750,223 A | * | 5/1998 | Tada et al. .................. 428/35.8 |
| 5,810,842 A | * | 9/1998 | Di Fiore et al. ............. 606/131 |
| 6,004,689 A | * | 12/1999 | Walker et al. ................ 429/53 |

FOREIGN PATENT DOCUMENTS

| | | |
|---|---|---|
| IT | 67279 | 10/1987 |
| IT | 1 184 922 | 10/1987 |
| JP | 403267053 | 11/1991 |

* cited by examiner

Primary Examiner—Glenn K. Dawson
(74) Attorney, Agent, or Firm—Foley & Lardner

(57) ABSTRACT

A dermabrasion apparatus operating by a flow of air and reducing substances conveyed by a pneumatic system through a handpiece. The apparatus comprises a housing, a vacuum pump, and an external tray inside of which a mixing bottle and a collecting bottle are provided. The apparatus further comprises at least one external source of pressurized sterilized air, or other suitable gas. The handpiece and the bottles are disposable sterilized components. Two or more of the components can be color-coded and sold in a kit.

1 Claim, 7 Drawing Sheets

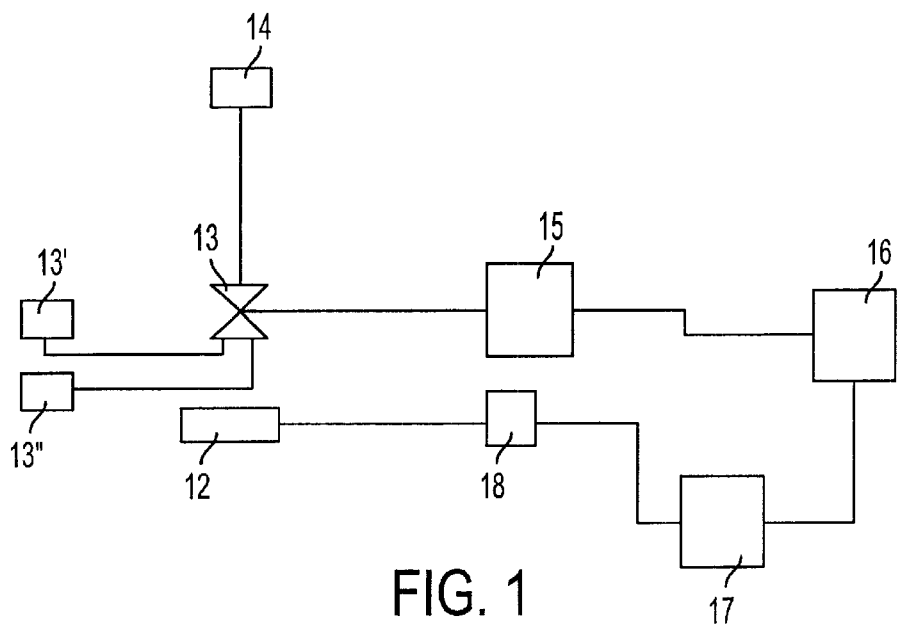
FIG. 1
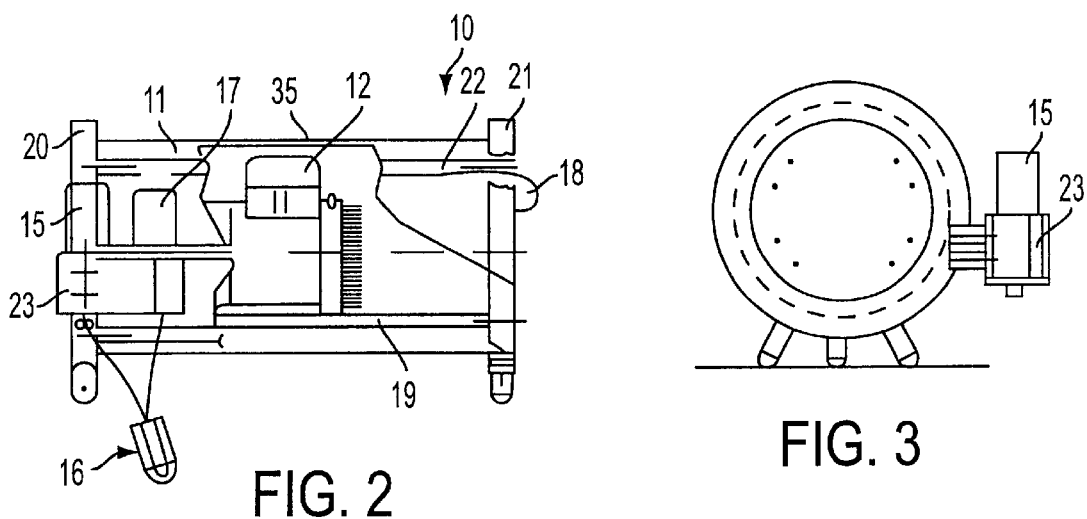
FIG. 2
FIG. 3

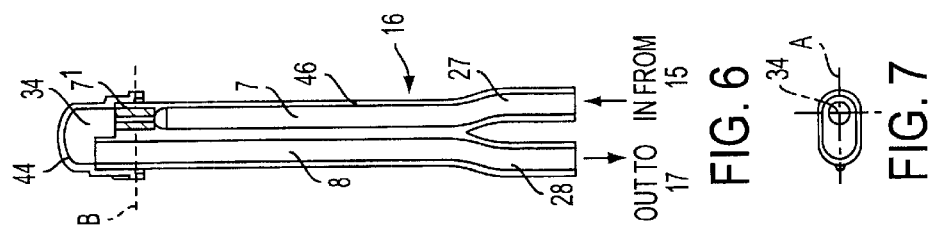
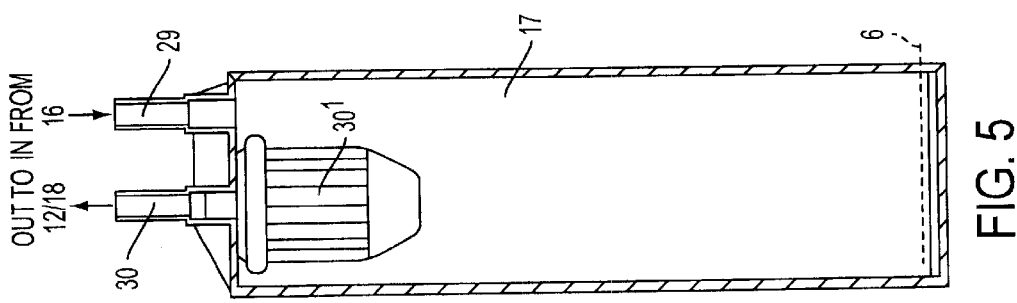
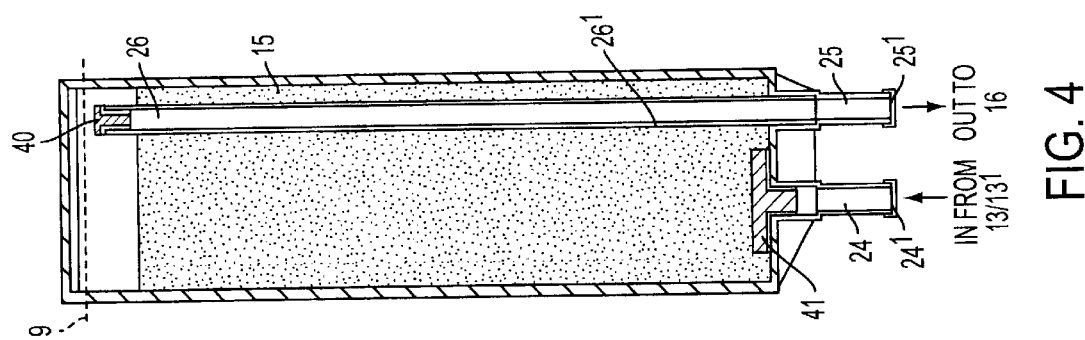

DERMABRASION BY A FLOW OF REDUCING SUBSTANCES AND HAVING DISPOSABLE STERILIZED COMPONENTS

RELATED APPLICATIONS

This application is a continuation-in-part of U.S. Ser. No. 08/496,470, filed Jun. 29, 1995, now U.S. Pat. No. 5,810,842, which is a continuation-in-part of U.S. Ser. No. 08/797,909 filed Feb. 10, 1997 now U.S. Pat. No. 6,120,512, which is a continuation-in-part of U.S. Ser. No. 09/088,873 filed Jun. 2, 1998 now abandoned, and U.S. Ser. No. 09/099,523 filed Jun. 18, 1998 now U.S. Pat. No. 6,306,141.

FIELD OF THE INVENTION

The present invention relates to the field of the cosmetic and microsurgical treatments. In particular, the present invention relates to a microdermabrasion apparatus and to the components making up the apparatus, operating by a pressurized flow of air and reducing substances, preferably corundum.

BACKGROUND OF THE INVENTION

Several technical solutions to produce a microdermabrasion apparatus are already known, all comprising vacuum means and/or pressurizing means which send a flow of air and reducing substances on a tissue portion to be treated and then remove from that portion the abraded particles. A drawback of such systems is that the sterility of the various components is not guaranteed, without the use of complicated and expensive processes.

Italian patent application FI94A000131, which corresponds to U.S. application Ser. No. 08/496,470 and is incorporated in its entirety herein by reference, describes a dermabrasion apparatus operating by a flow of reducing substances. The apparatus comprises a compressor, a vacuum pump, and three detachable one-piece components. The components include a mixing bottle, a collecting bottle for the abraded particles and a handpiece to touch the tissue to be treated. These components are preferably made of glass or plastic material and can be easily sterilized.

However, potential drawbacks of such an apparatus include the fact that the air pressurization is performed by a compressor placed inside the apparatus, making it necessary to sterilize the air because, during treatment, the compressor could be infected by bacteria which would be afterwards conveyed on the patient's skin by the pneumatic system. Furthermore, while the above-mentioned one-piece components are sterilized after the apparatus has been used, they do not guarantee proper sterility when the apparatus performs succeeding treatments on different patients. A further drawback is that contamination can occur when the mixing bottle is filled with new reducing substances or when the collecting bottle is cleaned of the abraded particles.

OBJECTS OF THE INVENTION

One object of the invention is to ensure the sterility of the apparatus components in all circumstances, for instance when sterilization means, such as UV rays or an autoclave, are not available. A further object of the invention is to obtain easy replaceable, low cost apparatus components.

SUMMARY OF THE INVENTION

The present invention provides a microdermabrasion apparatus having disposable sterilized components which include easily interchangeable one-piece blocks. Such components include an already filled mixing bottle containing the reducing substances, a collecting bottle for the abraded tissue particles, and a handpiece contacting the tissue during the treatment. The handpiece, the mixing bottle and the collecting bottle are manufactured and sealed in a sterilized environment. According to an embodiment of the invention the components are made of plastic material, preferably polycarbonate, in order to reduce costs, and to make them particularly suitable for disposable use. According to a further embodiment of the invention, after manufacturing, the components can be packed in sterilized packagings which include either a single component or a multi-component kit. In this way, contamination risks are reduced from the manufacturing through use of the components. In order to avoid contaminating the reducing substances, preferably corundum, with particles of the handpiece material abraded in use, the portion of the handpiece most subjected to the abrasion effect is an abrasion-proof block made of a suitably hard material, for example glass or ceramics. According to a further embodiment of the invention, the source of pressurized air, or of another suitable gas, is constituted by at least one disposable bottle of sterilized pressurized air. In this way, sterility is guaranteed to the apparatus components exposed to contamination risks for each treatment. A further advantage is low cost of production for such components.

DESCRIPTION OF THE DRAWINGS

These and other objects and advantages of the invention will become more fully apparent from the following detailed description when read in conjunction with the accompanying drawings with like reference numerals indicating corresponding parts throughout, and wherein:

FIG. 1 schematically shows the layout of the apparatus according to the invention;

FIG. 2 shows a side view of the apparatus according to the invention;

FIG. 3 shows a front view of the apparatus of FIG. 2;

FIG. 4 shows a preferred embodiment according to the invention of the mixing bottle filled with reducing substances;

FIG. 5 shows a preferred embodiment of the collecting bottle according to the invention;

FIG. 6 shows an embodiment of the contacting handpiece according to the invention, FIG. 7 shows a top view of the handpiece of FIG. 6;

DETAILED DESCRIPTION OF THE PREFERRED EMBODIMENTS

Figure 10:
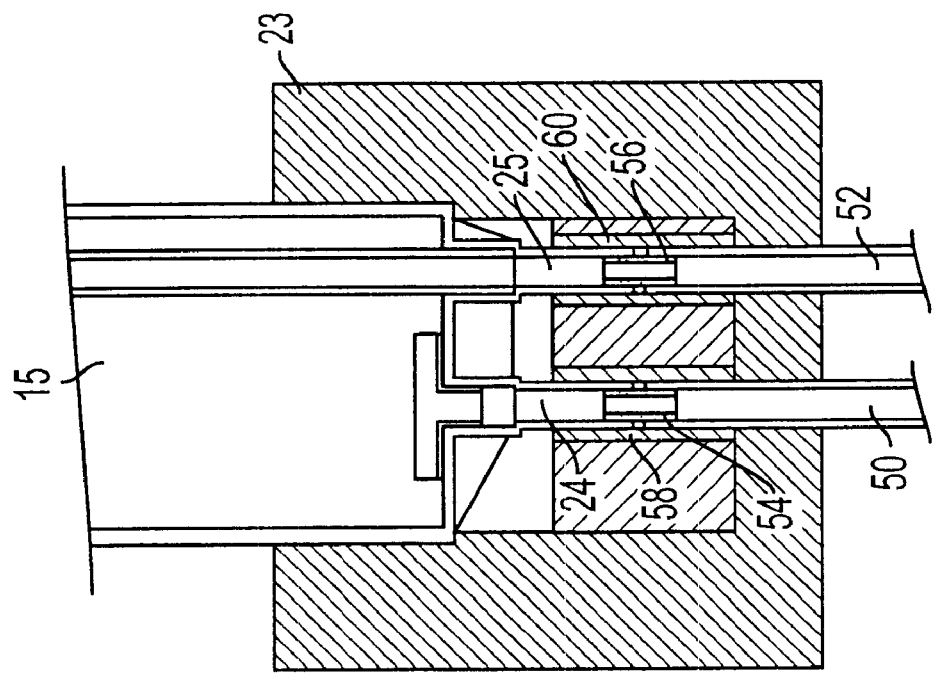
FIG. 10 shows the fitting of the mixing bottle onto the external tray according to the present invention.

Referring to FIGS. 1 and 2, a microdermabrasion apparatus 10 according to the invention comprises a housing 11, a vacuum pump 12, a mixing bottle 15 containing the reducing substances, for example corundum or aluminum oxide (sand-like substance), and a collecting bottle 17 to collect the reducing substances and the abraded tissue particles after use. As shown in FIG. 1, apparatus 10 is connected by a pneumatic system to a handpiece 16, which is intended to contact the tissue portion (e.g., skin of a patient) during treatment of a patient. The described embodiment also provides a valve 13 controlled by a switch 14, for example a treadle switch, able to switch the air inlet from two different sources 13', 13'. In a first example, the first source is a bottle of pressurized and sterilized air, and the second source is air at ambient pressure. In a further embodiment, the switching operates between two pressurized bottles feeding the sterilized air at different levels of pressure, so that a user can vary the abrasion efficiency of the apparatus according to the treatment requirements without interrupting the treatment. The same effect can be achieved by providing a single source with two outlet connections adjusted to output the air at different pressures. Downstream from the collecting bottle 17 and upstream from the vacuum pump 12, there is also provided a filter 18 to stop small particles flowing accidentally from the collecting bottle 17.

Figure 17:
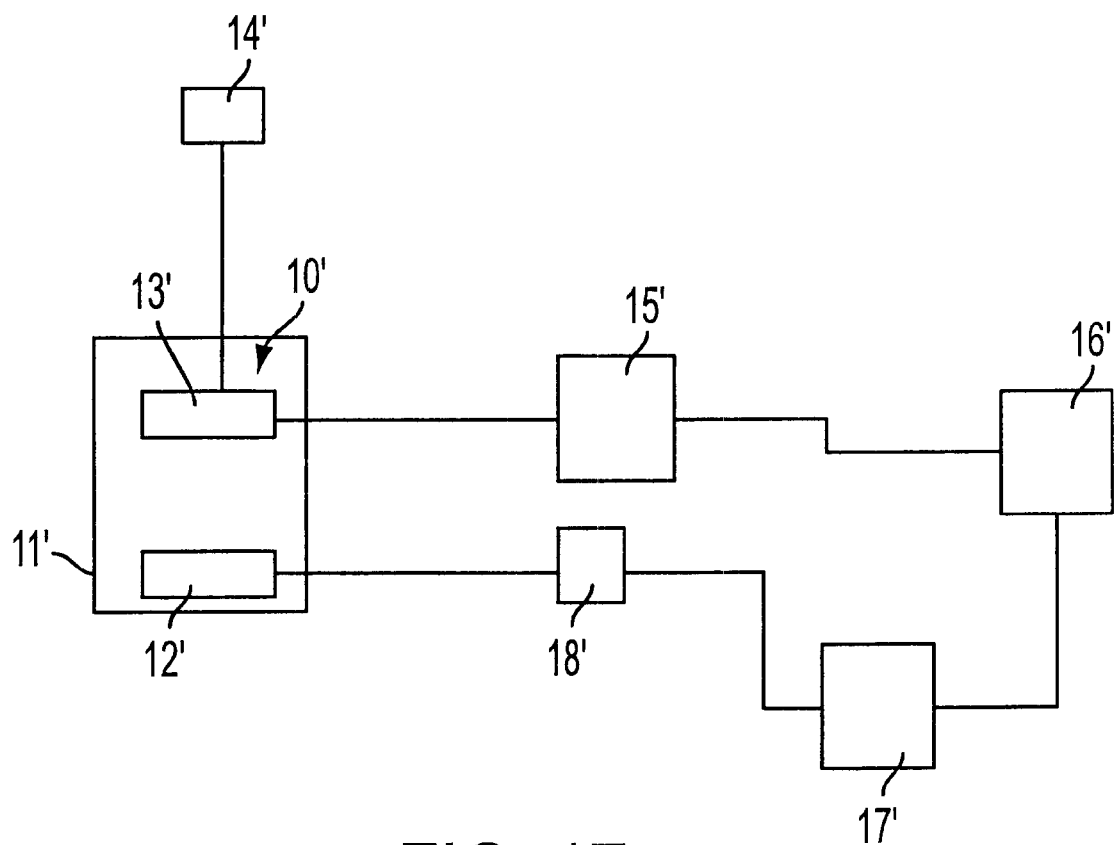
FIG. 17 schematically shows the layout of an alternative embodiment of the invention.

In an alternative embodiment, as shown in FIG. 17, equipment for microdermabrasion using a flow of a mixture of air and reducing substances, includes a casing 11' in which a vacuum pump 12' is placed and a compressor 13' is actuated by a control footswitch 14'. The equipment further comprises a mixing bottle 15' containing a mixture of air and reducing substances, a handpiece 16', and a collecting bottle 17'. The mixing bottle 15', the handpiece 16' and the collecting bottle 17' are contained in one cylinder block. The handpiece 16' is connected to the mixing bottle 15' by a first conduit, and to the collecting bottle 17' by a second conduit.

In this alternative embodiment, shown in schematic block diagram from in FIG. 17, a body machine 10', composed of an external casing 11' which has as its interior a vacuum pump 12', a compressor 13' with a control footswitch 14', and adjusting and control devices (not shown in FIG. 17), is provided.

The steps to be performed by an operator on traditional equipment or on equipment according to this alternative embodiment, are the following:
a) Switching "ON" of the equipment and initially adjusting the vacuum level desired.
b) Positioning the handpiece 16' on the area to be treated.
c) Actuating the compressor 13' through the footswitch 14' if a deep abrasion is required.

FIGS. 2 and 3 illustrate an embodiment of the housing 11, which includes a casing 35, preferably made of plexiglass, and a bar 19 supporting the vacuum pump 12, where lateral flanges 20, 21 are connected by threaded tie rod 22. Housing 11 further includes a tray 23, preferably an external tray, fixed to the flange 20 and housing the mixing bottle 15 and the collecting bottle 17. Flange 21 holds the filter 18 placed upstream from the vacuum pump 12. Referring to FIG. 4, the mixing bottle 15 is a substantially cylindrical one-piece block obtained, for example, by ultrasound welding along a horizontal junction line 9. In FIG. 4, the junction line 9 is shown near the top portion of the mixing bottle 15, to allow for simpler manufacturing of the pieces making up the mixing bottle 15. Of course, the junction line 9 can be placed at any other location of the mixing bottle 15, while remaining within the scope of the invention.

Mixing bottle 15 is provided with connection pipes 24, 25 connected respectively with valve 13, and with the pneumatic duct leading to the handpiece 16 according to the scheme of FIG. 1. Pipe connection 25 extends into the mixing bottle 15 with a suction tube 26 having a hole 26' (or aperture) near the bottom wall of mixing bottle 15, through which the reducing substances are introduced into the pneumatic system. Preferably, hole 26' is located at a position between $\frac{1}{10}$ and $\frac{3}{10}$ of the total height of the mixing bottle. This position of the hole 26' is high enough on the pipe connection 25 such that an air/corundum mixture that passes through the hole 26' and thereby into the pipe connection 25 is of sufficient density so as not to cause blockage of the hole 26'. Also, the position of the hole 26' is low enough on the pipe connection 25 such that air introduced into the mixing bottle 15 causes sufficient vibration or movement of the corundum inside the mixing bottle 15, so as to create a desired air/corundum mixture.

Figures 9A, 9B:
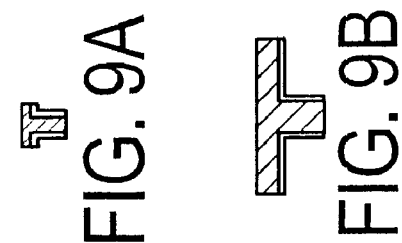
FIG. 9a shows one of the filters (or labyrinths) of the mixing bottle of FIG. 4.
FIG. 9b shows the other of the filters (or labyrinths) of the mixing bottle of FIG. 4.

Tube 26 and the inner end of the pipe connection 24 are provided with labyrinths 40, 41 schematically shown in FIGS. 9a, 9b, respectively. Labyrinths 40, 41 present a T section with radial passages through which the air can pass whereas there is avoided the accidental backflow of the corundum through the pipe 24 connection and the possible introduction of the same into the tube 26, during the transporting operation. Preferably, labyrinths 40, 41 have eight passages (or holes) symmetrically spaced on the top portion of thereof. Of course, other numbers of passages may be envisioned while remaining within the scope of the invention. Each passage preferably has a diameter of about 1 millimeter, so as to provide air bubbles of a size that causes sufficient vibration and movement of the corundum within the mixing bottle 15. The air bubbles output from each hole of labyrinth 41 move upwards as streamlets of air, and cause vibratory movement of the corundum. The T-shape of the labyrinth 41 is structured such that, during non-operational states (i.e., when the hole 34 is uncovered), the corundum in the mixing bottle 15 only moves part-way into the top-T portion of each T-shape passage, and does not move into the bottom-T portion of each passage. This is due primarily to the non-fluidity of the corundum, which tends to bunch up like sand and not flow readily unless provided with air under pressure. Thus, back-flow of the corundum into the connection tube 24 is effectively prevented.

According to the invention, the mixing bottle 15 is filled with the corundum in an aseptic environment and thereafter is closed, preferably by ultrasound welding, and then sealed by suitable plug 24', 25'. For example, each plug 24', 25' can have a bottom rubber layer which is pierced by the extremities of corresponding connecting junctions of the external tray 23 when the plugs 24', 25' are fitted into the external tray 23. Alternatively, each plug 24', 25' may comprise an aluminum foil or strip, which is punctured when the mixing bottle 15 is fitted into the external tray 23. In such a way, the mixing bottle 15 is connected with the valve 13 and with the downstream handpiece 16.

FIG. 10 shows the fitting of the mixing bottle 15 onto the external tray 23. In FIG. 10, the external tray 23 includes two connection pipes 50, 52, which are preferably made of a silicone-based material, or plastic. Pipes 50, 52 are flexible and preferably transparent in color. Disposed inside pipes 50, 52 are metal rings 54, 56, respectively. Disposed outside pipes 50, 52 are rubber seals 58, 60 which are snugly fit around pipes 50, 52. Rubber seals 58, 60 provide a strong air-tight seal when connection pipes 24, 25 are fitted against pipes 50, 52, respectively. When mixing bottle 15 is fitted onto external tray 23, the connection pipes 24, 25 are moved downward towards the pipes 50, 52, so as to cause piercing of the plugs 24', 25' by metal pipes 54, 56. That way, an air-tight connection is provided.

Referring to FIG. 6, the handpiece 16 according to a first configuration comprises a substantially elliptical one-piece block having the upper portion in the shape of a hollow elliptical cap 44. Handpiece 16 is provided with an inlet connection 27 corresponding to an inner tube 7 through which the air and the reducing substances enter into the elliptical cap 44. After use, the reducing substances are removed from the elliptical cap 44 by a second tube 8 and a corresponding outlet connection 28. The handpiece elliptical cap 44 presents an opening 34, the rim of which defines the patient's tissue portion impinged upon by the reducing substances ejected from tube 7.

Figures 8A, 8B:
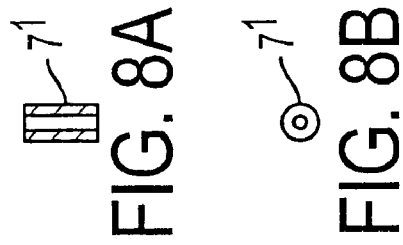
FIGS. 8a, 8b show different views of the abrasion-proof block of the handpiece of FIG. 6.
Figure 13:
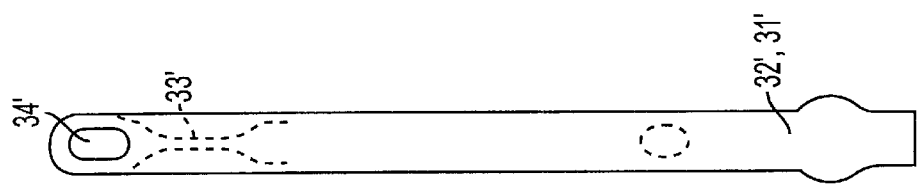
FIGS. 12 and 13 show different views of a handpiece according to an alternative embodiment.
Figure 12:
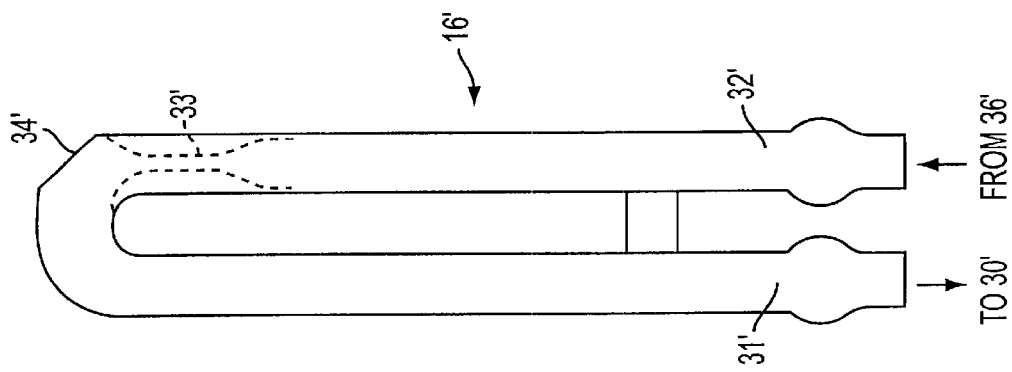

According to the invention the upper end of tube 7, which is the part subjected to the highest abrasion, is provided with an insert block 7', shown in FIGS. 8a, 8b. Block 7' is a cylinder having an internal diameter smaller than a diameter of the tube 7 to achieve a smaller flow area and thus increase the flow rate of the reducing substances. Block 7' is made of a hard material, preferably glass or ceramics. In the described embodiment, handpiece 16 has two half parts 46 symmetrical with respect to line A of FIG. 7 and manufactured, for example, by injection molding, together with the corresponding half parts of tubes 7, 8. Before assembling, block 7' is inserted into the upper end portion of tube 7 and the spherical cap 44 is attached so that the opening 34 corresponds to the block 7'. That is, an air/corundum mixture output from mixing bottle 15 goes through inlet connection 27, through inner tube 7 and then through insert block 7', and finally contacts a patient's skin (not shown) covering opening 34. The covering of the opening 34 creates a vacuum, so as to cause the air/corundum mixture to flow towards the patient's skin. The air/corundum mixture under pressure causes abrasion of the patient's skin, and a skin/corundum/air mixture is passed through tube 8, through outer connection 28, and is collected by collecting bottle 17. After attachment of the elliptical cap 44, the assembly is closed, for example by ultrasound welding along line A and line B between the elliptical cap 44 and the lower body 46 (see FIGS. 6 and 7). Alternatively, the elliptical cap 44 is welded to the lower body 46 by a single injection molding operation. In the alternative configuration, the handpiece 16 corresponds to a unitary piece or monoblock, such as the U-shaped monoblock shown in FIG. 6 of the drawings, or the one shown in FIGS. 12 and 13. As shown in these figures, the reducing material discharge most of their kinetic energy contacting the area of skin to be treated, which "closes" an exit window 34'. After having executed the abrasive operation, the mixture of air and reducing materials, which contains some skin fragments, is evacuated through the exit pipe 31' toward the collecting bulb 17', such as the monoblock collecting bulb 17' seen in FIG. 14. The handpiece 16' can be made by folding a pipe (e.g., comprising tempered pyrex glass) into a U-shape. The elliptic shaped exit window 34' is placed, after folding the pipe, in front of the nozzle 33' and may be raked at an angle between 30 degrees and 60 degrees, respectively, to a central symmetrical axis of the handpiece 16'.

Advantageously, the relation between length and diameter of a groove of the nozzle 33', and between a length of the handpiece 16' and a diameter of the handpiece pipe, should be between 5 and 30.

The composition of tempered pyrex glass and the geometry of the handpiece 16' allow, together with the handpiece lightness, increased maneuverability to treat the skin and increased operative sensitivity. The handpiece 16' sliding over the skin occurs in a soft and regular way. Due to the geometry of the handpiece 16' and the exit window 34', the regeneration of reducing substances is almost total and consequently their deposit on the skin after the treatment is much reduced. This fact allows a simple and fast cleaning of the treated part.

Figure 11:
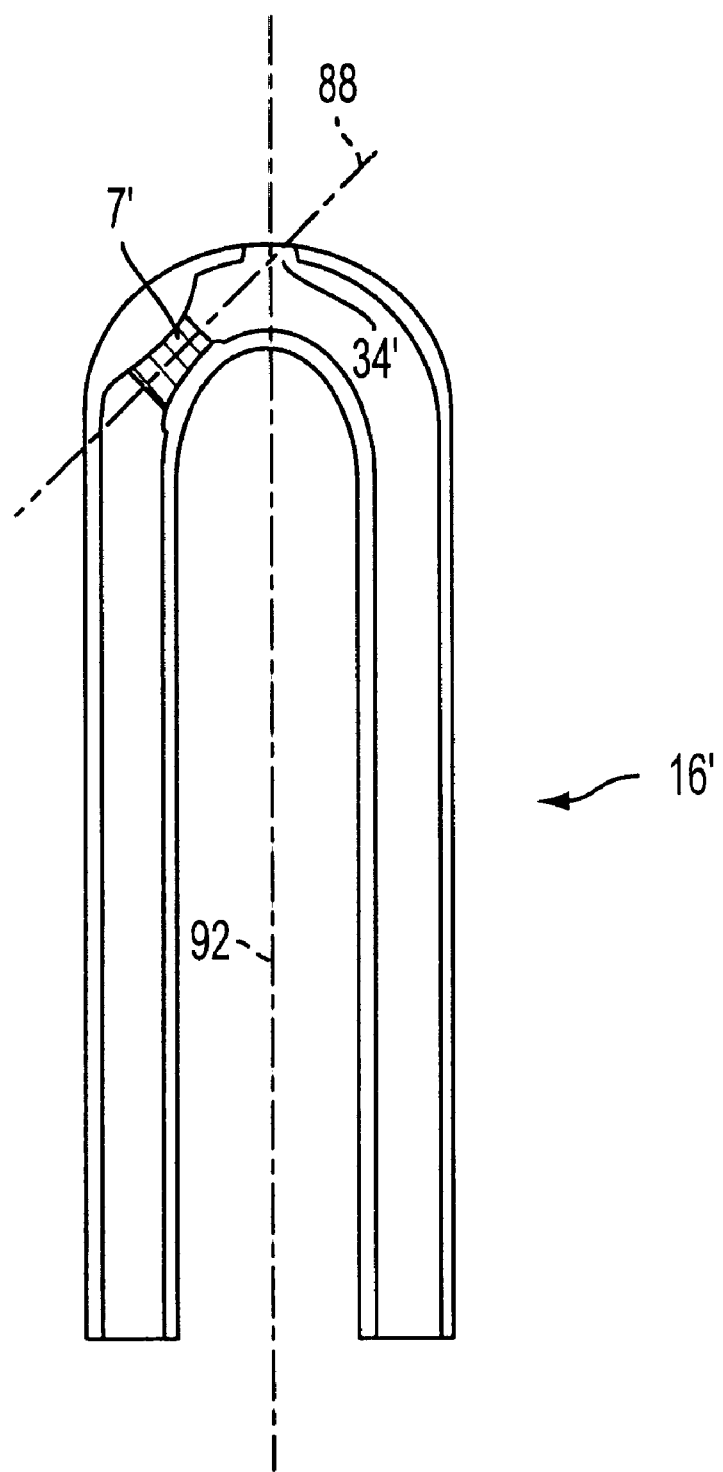
FIG. 11 shows another embodiment of the contacting handpiece according to the present invention.

In another alternative configuration, as shown in FIG. 11, the contacting handpiece 16' is configured to have the insert block 7' situated in a curved portion at the top of the handpiece 16'. By this configuration, the air output from the insert block 7' is directed towards the opening 34', with the air direction being shown by the dashed line 88. The opening 34' is positioned at a substantially central position of the handpiece 16'. A longitudinal axis of the handpiece 16' that bisects the handpiece 16' is shown by dashed line 92.

Referring to FIG. 5, there is shown the collecting bottle 17, placed downstream of the handpiece 16 and upstream of the vacuum pump 12, according to the pneumatic system scheme of FIG. 1. Collecting bottle 17 has a cylindrical hollow one-piece block provided with two upper connections 29, 30, the first operating as inlet for the reducing substances from handpiece 16, the second as a passage for the air aspirated by vacuum pump 12. Connection 30 is provided with an air filter 30' in order to avoid the passage of used reducing substances and of tissue abraded particles towards the vacuum pump 12.

In the described embodiment, collecting bottle 17 is assembled by welding (preferably ultrasound welding) along line 6, the upper portion including connections 29, 30. The welding is preferably to connect a small portion of the collecting bottle 17 to the rest of the collecting bottle 17. That way, it is easier to manufacture the two pieces making up the collecting bottle 17. Downstream from the collecting bottle 17 is disposed a filter 18 for filtering small particles passed through the filter 30' and conveyed towards vacuum pump 12. Filter 18 is preferably disposed immediately downstream from collecting bottle 17. Advantageously, the connections of collecting bottle 17 and handpiece 16 are provided with plugs, similar to previously described plugs 24', 25' which are intended to seal both collecting bottle 17 and handpiece 16 until their initial use, and to allow a quick and easy connection to the pneumatic system. After manufacture, the mixing bottle 15, the collecting bottle 17 and the handpiece 16 can be packaged, individually or in a kit including either all three components or at least the handpiece and collecting bottle, in sterilized packaging. The connection tubes can optionally be included in the kit. By having a disposable mixing bottle 15 that is manufactured and sent with seals 24', 25' to a user or operator, the user does not have to worry about bacteria or the like entering the mixing bottle 15, since it has already been sterilized (by gamma rays, for example) during manufacturing. Also, each mixing bottle may also have a silica-gel package or other type of desiccant disposed within the mixing bottle along with the corundum. The silica-gel package keeps any moisture from forming inside the mixing bottle, thereby keeping the corundum from clumping up and causing problems in the system. That way, a heating element to keep the corundum dry inside the mixing bottle is not required in the present invention.

Figure 14:
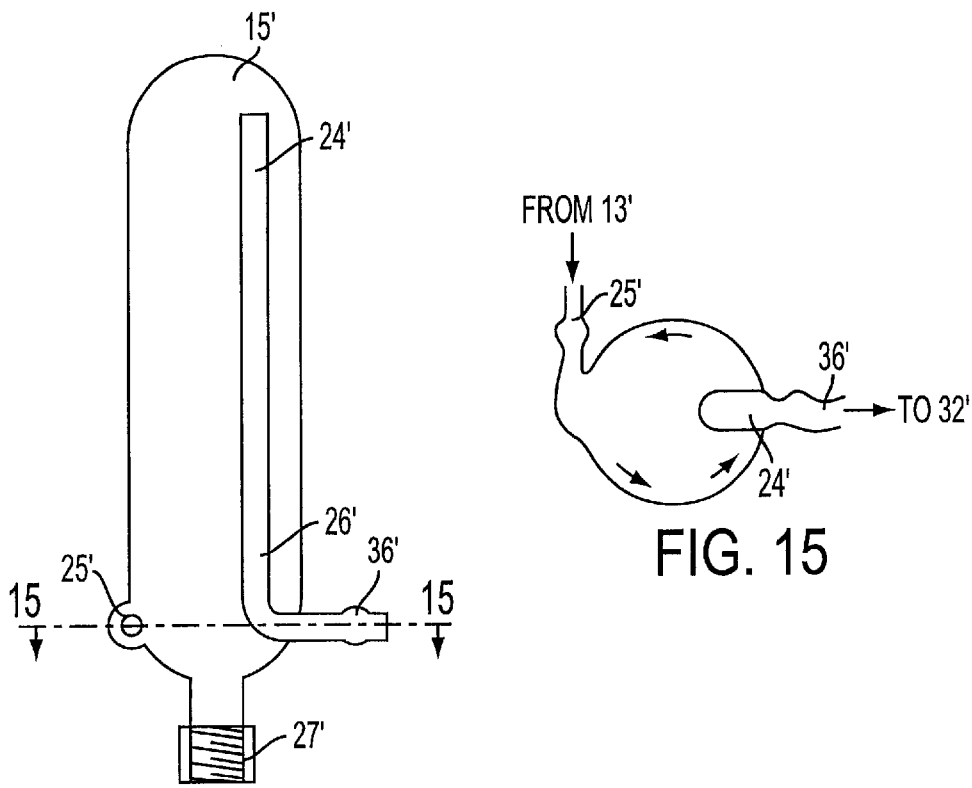
FIGS. 14 and 15 show different views of a mixing bottle according to an alternative embodiment.
Figure 15:
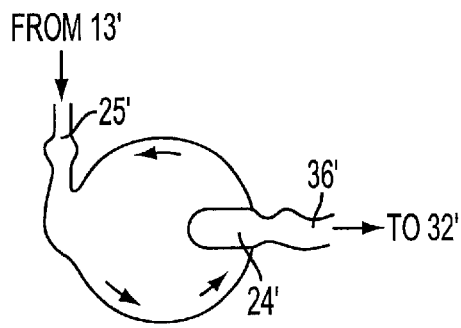
Figure 16:
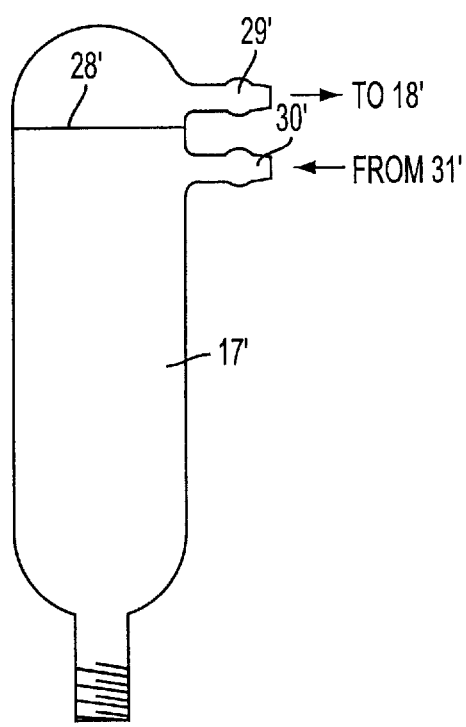
FIG. 16 shows a collecting bottle according to an alternative embodiment.

FIGS. 14 and 15 show a mixing bottle according to another embodiment, and FIG. 16 shows a collecting bottle according to another embodiment. The mixing bottle and the collecting bottle of this other embodiment are contained in a one cylinder block. When exposed to the skin tissue of a patient's skin, the mixture of air and reducing materials with the removed skin fragments is vacuumed into the collecting bottle 17'. At the bottom of the collecting bottle 17', crystals and tissue fragments are deposited. A porous septum 28' (comprising, for example, sintered glass) of the collecting bottle 17' separates the vacuum pipe 29' from the crystal return pipe 30'. The porous septum 28' does not allow the reducing material mixed with the skin fragments to reach an impeller of the vacuum pump 12'. Safety filtering is effected through a feedback air filter placed downstream from the collecting bottle 17'. The filter does not allow the skin fragments, which escape into the sintered glass porous septum 28' from the collecting bottle, to enter the body machine.

In the mixing bottle as shown in FIGS. 14 and 15, the flow of compressed air may be directed to the interior of the mixing bottle 15' according to a direction tangential to the mixing bottle's wall. In this way, the reducing substances act according to directions concentric to the main symmetrical axis of the mixing bottle 15', thus obtaining a substantial kinetic energy before entering the vacuum hole 26'. This method of mixing of air with reducing substances creates an improved abrasive action. The mixing bottle 15', besides containing reducing substances ready to use, contains a mixture of air and reducing substances. The mixing bottle 15' comprises a single element in a glass or plastic material. In this regard, the mixing bottle 15', the collecting bottle 17', and the handpiece 16' each form a "monoblock", where monoblock is defined as a constructive component composed of one or more integral parts, without the use of mobile mechanical connections and without it being possible to split the component upon into multiple subparts.

Referring to FIGS. 2 and 14–16, the mixing and collecting bottles 15', 17' of the another embodiment are releasably supported by the external tray (or tumbler) 23, in the same manner as how the mixing and collecting bottles 15, 17 of the first embodiment are releasably supported. This allows, when necessary, an immediate replacement of the mixing and collecting bottles 15', 17'. In fact, it is enough to disconnect the pipes and pull out the mixing and collecting bottles 15', 17' from the external tray 23.

The one-piece blocks according to the invention constitute a kit of disposable components which does not require the steps of: filling the mixing bottle with the reducing substances, cleaning the abraded particles from the collecting bottle and handpiece, or sterilizing critical parts of the apparatus. These steps were required in conventional devices, and represented additional time and money spent to achieve treatment safety. In the present invention, it is also possible to set an expiration time for the sterility condition of the blocks individually or as contained in the unique kit packaging. Upon reaching the expiration time, all critical parts of the apparatus can be safely and quickly replaced due in part to the described sealing plugs 24, 25, used to connect handpiece 16 with the mixing bottle 15 and the collecting bottle 17. The blocks can be made of any suitable plastic or vitreous material. A polycarbonate is preferred because it is a low cost material and can be sterilized by an autoclave when reuse of one or more components is needed. Alternatively, a polystrene structure or the like may be used. According to a further feature of the invention, the kit components can be manufactured in different colors in order to allow a better identification of their functions by the user, or can be transparent to allow the user to visually detect any contamination particles remaining after sterilization.

What is claimed is:

1. A microdermabrasion apparatus, comprising:

a housing;

a mixing bottle coupled to the housing, the mixing bottle having a cylindrically-shaped sidewall, the mixing bottle having a first port provided on the sidewall, the first port being a port through which air is provided to the mixing bottle to thereby interact with reducing substances disposed within the mixing bottle to thereby provide an air/reducing substances mixture;

a collecting bottle coupled to the housing; and a handpiece extending between the mixing bottle and the collecting bottle, wherein the mixing bottle is configured to provide the air/reducing substances mixture to the handpiece, wherein the handpiece is configured to be applied to a patient so as to remove skin fragments from the patient, wherein the collecting bottle is configured to receive a combination of the skin fragments and the air/reducing substances mixture from the handpiece, and wherein the air is provided to an interior of the mixing bottle in a direction tangential to the sidewall of the mixing bottle, to thereby increase an abrasive action of the air/reducing substances mixture as the air/reducing substances mixture exits the mixing bottle and moves into the handpiece.

* * * * *